US010603108B2

(12) United States Patent
Lutschounig et al.

(10) Patent No.: US 10,603,108 B2
(45) Date of Patent: Mar. 31, 2020

(54) SKIN TREATMENT SYSTEM

(71) Applicant: KONINKLIJKE PHILIPS N.V., Eindhoven (NL)

(72) Inventors: Mario Arnold Lutschounig, Eindhoven (NL); Christian Mikula, Eindhoven (NL); Walter Julius Weichsler, Eindhoven (NL); Rene Gasser, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 21 days.

(21) Appl. No.: 15/664,465

(22) Filed: Jul. 31, 2017

(65) Prior Publication Data
US 2017/0325888 A1 Nov. 16, 2017

Related U.S. Application Data

(63) Continuation of application No. 13/823,616, filed as application No. PCT/IB2011/054376 on Oct. 5, 2011, now Pat. No. 9,724,160.

(30) Foreign Application Priority Data

Oct. 25, 2010 (EP) .................... 10188690

(51) Int. Cl.
*A61B 18/20* (2006.01)
*H05B 41/30* (2006.01)
(Continued)

(52) U.S. Cl.
CPC ........... *A61B 18/203* (2013.01); *H05B 41/30* (2013.01); *A61B 2017/00154* (2013.01); *A61B 2018/00476* (2013.01); *A61N 2005/0654* (2013.01)

(58) Field of Classification Search
CPC ............ H05B 41/30; A61N 2005/0654; A61B 18/203; A61B 2017/00154; A61B 2018/00476
(Continued)

(56) References Cited

U.S. PATENT DOCUMENTS 4,745,613 A * 5/1988 Tye ................. H01S 3/092
315/160
4,853,600 A * 8/1989 Zeltner ................. H05B 41/32
315/241 P
(Continued)

FOREIGN PATENT DOCUMENTS

JP 2008010327 A 1/2008
WO 2005036745 A2 4/2005
(Continued)

OTHER PUBLICATIONS

Informa Healthcare, "Journal of Cosmetic and Laser Therapy" Jan. 1, 2007. pp. 139-147.
(Continued)

*Primary Examiner* — Carl H Layno
*Assistant Examiner* — Dacheng Xie

(57) ABSTRACT

A method of operating a flashlamp in a skin treatment system comprises the steps of charging capacitor, discharging the capacitor through a flashlamp, and interrupting the discharge of the capacitor through the flashlamp at a predetermined time based on at least one condition caused by the discharge of the capacitor through the flashlamp.

19 Claims, 5 Drawing Sheets

(51) Int. Cl.
    *A61B 17/00* (2006.01)
    *A61N 5/06* (2006.01)
    *A61B 18/00* (2006.01)

(58) Field of Classification Search
    USPC .................................................. 607/86–94
    See application file for complete search history.

(56) References Cited

U.S. PATENT DOCUMENTS

| | | | |
|---|---|---|---|
| 5,735,844 | A | 4/1998 | Anderson et al. |
| 5,883,471 | A | 3/1999 | Rodman |
| 6,187,001 | B1 | 2/2001 | Azar |
| 7,108,689 | B2 | 9/2006 | Eckhouse |
| 7,491,222 | B2 | 2/2009 | Holjo |
| 9,132,279 | B2 | 9/2015 | Roersma |
| 2005/0045189 | A1 | 3/2005 | Jay |
| 2005/0056786 | A1 | 3/2005 | Shepard |
| 2005/0057180 | A1 | 3/2005 | Changaris |
| 2005/0177141 | A1 | 8/2005 | Davenport |
| 2005/0245997 | A1 | 11/2005 | Holjo et al. |
| 2006/0206173 | A1* | 9/2006 | Gertner ............... A61N 5/0616 607/88 |
| 2009/0059159 | A1* | 3/2009 | Howell ................ G02C 11/00 351/41 |
| 2009/0093799 | A1* | 4/2009 | Davenport .......... A61N 5/0616 606/9 |

FOREIGN PATENT DOCUMENTS

| | | |
|---|---|---|
| WO | 2005048808 A2 | 6/2005 |
| WO | 2007113817 A2 | 10/2007 |
| WO | 2009118617 A1 | 10/2009 |
| WO | WO 2009118617 A1 * | 10/2009 ........... A61N 5/0617 |

OTHER PUBLICATIONS

Cyden Ltd, "IFL I200 System User Manual", Feb. 23, 2005, pp. 1-44.
Clement, Daniel & Trelles, "Optimising the Design of a Broad-Band Light Source for the Treatement of Skin", Journal of Cosmetic and Laser Therapy, 2005- pp. 177-189.
Hughes, Scott, Lecture 7: Current, Continuity Equation, Resistance, Ohm's Law , MIT Department of Physics, pp. 63-71, Feb. 27, 2005.

* cited by examiner

SKIN TREATMENT SYSTEM

CLAIM OF PRIORITY

This application claims priority to, and the benefit of the earlier filing date of, that patent application filed on Mar. 14, 2013 and afforded Ser. No. 13/823,616 and issued as U.S. Pat. No. 9,724,160, which is a National Stage Entry of PCT/IB11/54376, filed on Oct. 5, 2011, the contents of all of which are incorporated by reference, herein.

FIELD OF THE INVENTION

The present invention relates in general to a skin treatment system, especially a hair removal system, on the basis of intense pulsed light. In the following, the present invention will be specifically explained for a hair removal system, but the gist of the invention can be more generally applied in skin treatment systems.

BACKGROUND OF THE INVENTION

The desire to remove (human) body hair is quite old, and many systems have been developed for meeting this desire. For instance, there are mechanical systems operating on the basis of mechanically cutting or pulling out the hairs. A more recent development is applying light pulses of a high intensity to a portion of the skin where the hair is to be removed. This technique is known per se, so that an elaborate explanation may be omitted here. Suffice it to say that light energy is absorbed in the skin and destroys the follicles so that the hair will fall out. An advantage is that the hair removal is more permanent: it takes longer before hairs return, or they do not return at all. By way of example of prior art, reference is made to U.S. Pat. No. 5,735,844.

In the system described in said prior art document, the intense light pulse is generated by a laser device. This, however, requires the use of laser. The present invention is specifically related to a hair removal system comprising a flashlamp as the light source.

SUMMARY OF THE INVENTION

In light pulse hair removal systems, there is a problem relating to temperature. In the case of flashlamps, the light pulse contains energy in a relatively wide spectral region, but not all spectral portions contribute to the destruction of hair follicles to the same extent. Thus, energy is invested in light frequencies that are not effective or not sufficiently effective in the process of hair removal. Further, not all energy is absorbed in the skin.

Further, it has been found that people respond differently to the light treatment, possibly caused by differences in skin characteristics. People who have a more sensitive skin type may, in general, experience a pain sensation already in circumstances where other persons do not.

Generally speaking, it is possible to divide the energy in a light pulse into three portions: 1) reflected by the skin; 2) absorbed by the skin but not effective in hair removal; 3) absorbed by the skin and effective in hair removal. Further, there will also be an energy loss in the conversion from electrical power to light power, which, together with the rejected light energy, will contribute to heating the apparatus or parts of it. The energy absorbed in the skin will cause a temperature rise in the skin. Now, on the one hand, the energy input into the skin should be sufficiently high to cause the destruction of the follicles and hence the falling out of hair, but on the other hand the thermal effects should be limited so as to prevent or in any case limit possible pain sensations.

More in general, there is a desire to limit energy consumption while retaining or even improving the hair removal efficiency.

When operating a hair removal system with a flashlamp, the light pulse is typically generated by discharging a capacitor, resulting in a pulse-shaped current through the lamp. The present invention is based on the insight that the momentary frequency spectrum of the light generated by the flashlamp depends on the momentary current density in the flashlamp, and further that the momentary current density varies with time, first quickly rising to a maximum and then slowly falling back to zero. The present inventors have realised that, with time, the reducing current density in the lamp causes the spectral distribution to gradually shift to higher frequencies. Based on this understanding, in one aspect of the present invention, the current pulse in the lamp is interrupted when the current density in the lamp drops below a certain level.

In another approach, the current intensity is set to be relatively high, and the current pulse in the lamp is interrupted when the total energy applied to the skin reaches a predetermined maximum value.

Further advantageous elaborations are mentioned in the dependent claims.

BRIEF DESCRIPTION OF THE DRAWINGS

These and other aspects, features and advantages of the present invention will be further explained by means of the following description of one or more preferred embodiments with reference to the drawings, in which same reference numerals indicate same or similar parts, and in which.

DETAILED DESCRIPTION OF THE INVENTION

Figure 1:
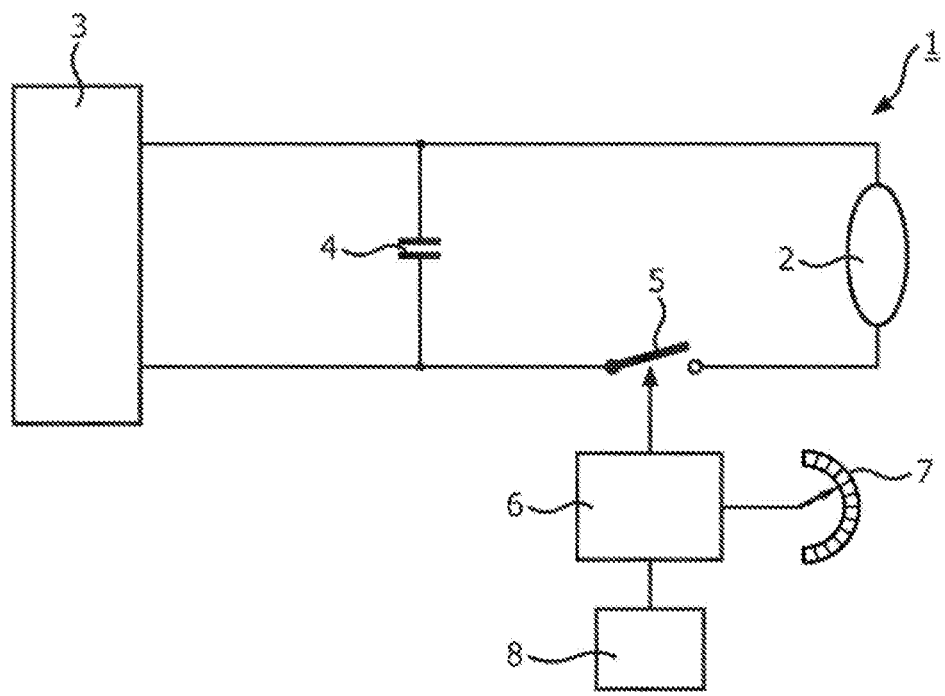
FIG. 1 schematically shows an electrical block diagram of a skin treatment system.

FIG. 1 schematically shows an electrical block diagram of a skin treatment system 1 according to the present invention, comprising a flashlamp 2. The flashlamp 2 is a discharge lamp, including a gas-filled vessel with two electrodes, as known per se. Although other types of flashlamps are possible, the flashlamp 2 typically is a xenon discharge lamp. A discharge capacitor 4 is mounted in parallel with the lamp 2, with a controllable switch 5 arranged in a current path between the lamp 2 and the capacitor 4. The capacitor 4 is supplied from a power source 3, typically a voltage source. The controllable switch 5 is controlled by a control device 6, for instance a microprocessor or the like.

Figure 2:
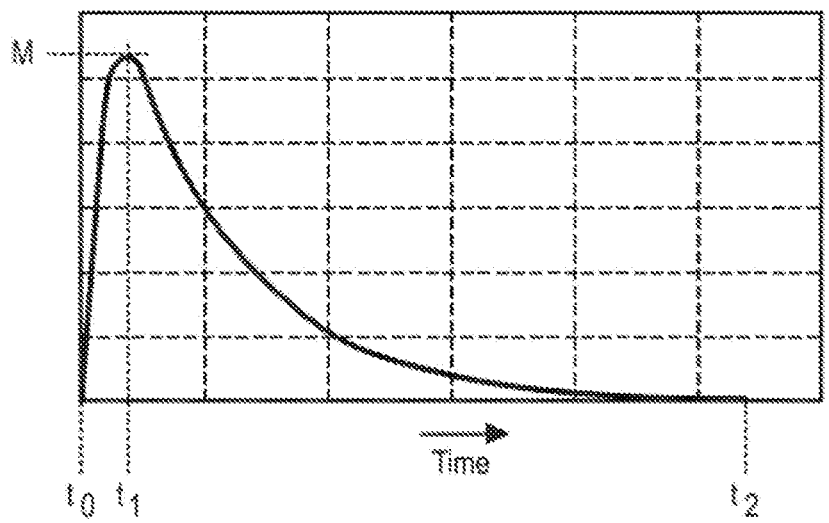
FIG. 2 is a graph showing lamp current density as a function of time for an uninterrupted free discharge.

FIG. 2 is a graph, showing lamp current density as a function of time, for illustrating prior art operation of such a flash lamp. First, the capacitor 4 is charged from the source 3. The switch 5 is open (i.e. non-conductive). At a certain moment t0, the control device 6 closes the switch 5 and an ignition circuit (not shown) causes ignition of the lamp. With the lamp ignited, the capacitor can discharge its energy over the lamp (discharge operation). The current density quickly rises to a maximum M, that is reached at time t1, and then slowly, exponentially, falls back to zero, which situation is reached at time t2. In theory, with a true exponential decay, the level of zero is never reached, but in practice the discharge extinguishes when the current drops below a minimum level required for maintaining the discharge. The moment when this happens will be indicated as "natural extinction time".

For repeating the above cycle, the switch 5 is first opened again so as to allow the capacitor 4 to be charged again. If desired, a second controllable switch may be arranged in the connection between voltage source and capacitor, which is only closed for charging the capacitor, but this is not shown for the sake of simplicity.

The precise values of t1 and t2, and the precise value of the current maximum M, depend inter alia on the precise characteristics of the lamp (such as gas filling, size), of the capacitor (such as capacitance), of the current discharge loop (resistance, inductance, capacitance) and of the power source (such as charge voltage).

It has been established that, in order to avoid undesirable effects such as pain or a burning sensation, the total amount of energy applied to the skin should not exceed a predetermined maximum $E_M$, which maximum may depend on skin type. Typical values for such a maximum are in the range of 3-6 Joule/cm$^2$. In the prior art design of a skin treatment system, the capacitor 4 is selected, depending on the type of lamp 2, such that in a free, uninterrupted discharge (see FIG. 2, from t0 to t2) the total amount of energy applied to the skin does not exceed said predetermined maximum $E_M$. A system according to such design will be indicated as a "nominal" system. With reference to FIG. 1, it is noted that the system, when the capacitor 4 has been charged to a voltage $V_0$ provided by the source 3, contains an energy Ec according to the formula $Ec=0.5 \cdot CV_0^2$, with C being the capacitance of the capacitor 4. When the capacitor has discharged completely at time t2, this energy has been inputted into the lamp, and the lamp has applied this energy to the skin. This applies if losses may be ignored, which in practice is not realistic: in practice, only a certain percentage of the electrical energy is actually applied to the skin. Thus, in a formula, this may be approximated as $E_{SKIN}=\alpha \cdot Ec$, with α expressing the ratio between electrical discharge energy Ec and energy $E_{SKIN}$ applied to the skin. In the following, for the sake of explanation, it will be assumed that α is constant. It follows, in the nominal design, that $E_{SKIN}=E_M=\alpha \cdot 0.5 \cdot C_0 V_0^2$.

Figure 3:
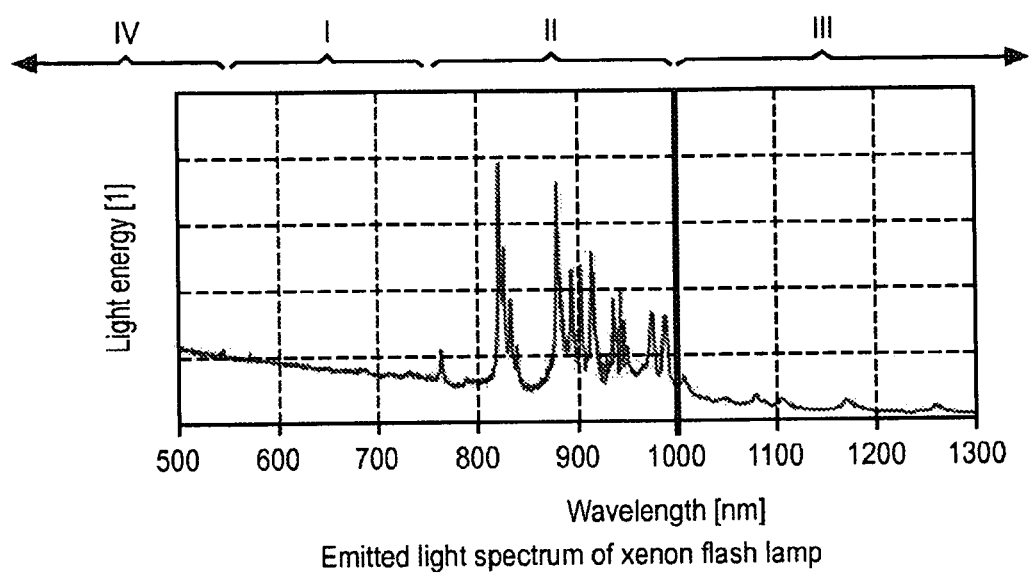
FIG. 3 is a graph showing an energy spectrum of a xenon flash lamp.

The discharge current will cause the lamp 2 to generate a pulse of intense light, as is known per se. The generated light is not monochromatic, but contains contributions in a large spectral region. FIG. 3 is a graph showing an illustrative energy spectrum of an exemplary xenon flash lamp. The vertical axis represents the total amount of energy (arbitrary units) emitted by the light pulse at a certain wavelength (horizontal axis, in nanometers).

FIG. 3 also shows that, for hair removal, basically four spectral regions can be distinguished, it being noted that the exact borderlines are not sharply defined:

a first region I is the spectral range from roughly about 550 nm to roughly about 750 nm, that contains the wavelengths useful for epilation;

a second region II is the spectral range from roughly about 750 nm to roughly about 950 nm/1000 nm, that contains the wavelengths that are still useful although to a lesser extent;

a third region III is the spectral range from roughly about 950 nm/1000 nm and higher: these are wavelengths that are actually undesirable because they have less effect in the follicle destruction but can cause harmful effects such as pain and/or burning;

a fourth region IV is the spectral range from roughly about 550 nm and lower: these are wavelengths that are actually undesirable because they can easily cause damage to the skin.

It can be seen that the energy spectrum of the light pulse from a xenon lamp has emission lines in the second region; a further emission line at about 1400 nm is not shown in this graph.

The spectrum shown in FIG. 3 is the overall spectrum, i.e. integrated over time from t0 to t2. However, since the spectrum depends on current density while the current density varies with time, also the spectrum varies with time. Roughly, it can be said that the relative energy distribution in the spectrum is concentrated at shorter wavelengths for higher current densities, and is concentrated at longer wavelengths for lower current densities. This phenomenon is known per se, and is for instance illustrated in FIGS. 11-14 of US patent application 2005/0177141. In this document, the current density in the lamp is controlled in order to obtain a desired energy spectrum depending on skin type of the treated person.

Figure 4:
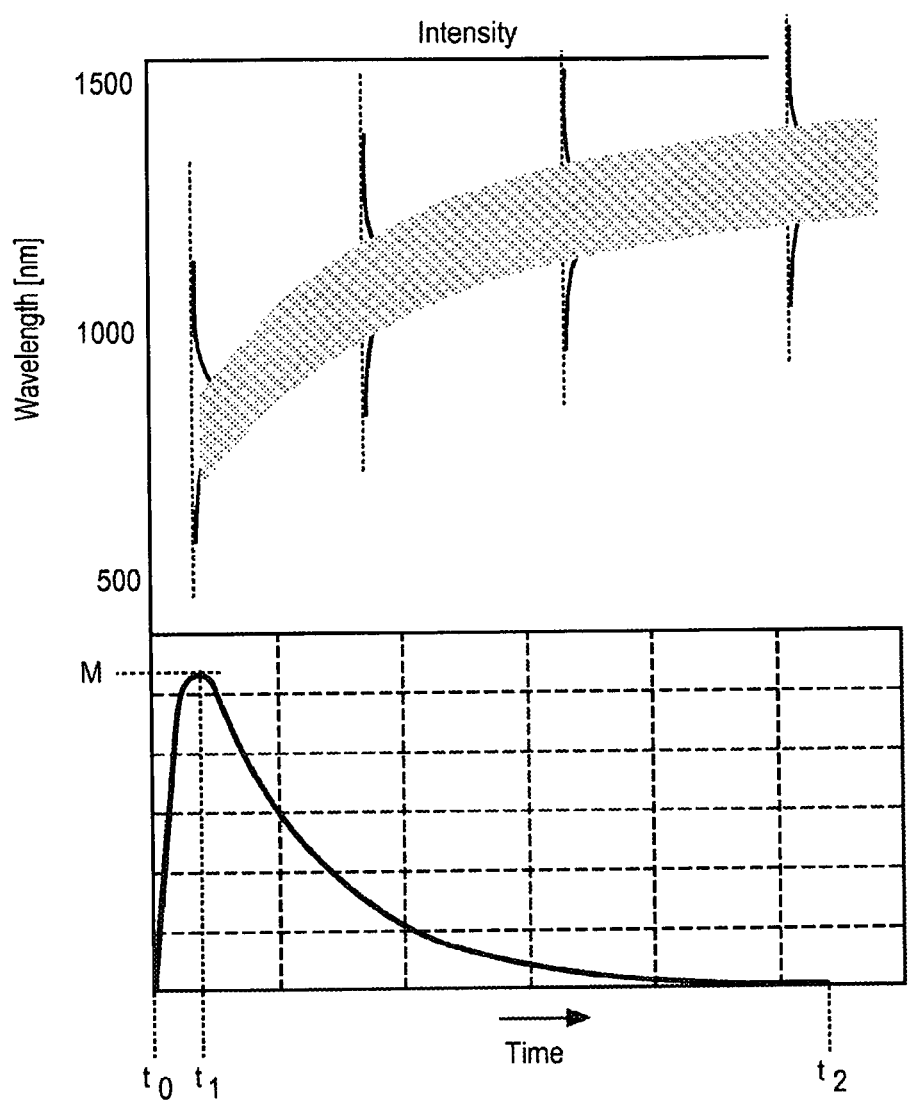
FIG. 4 is a graph schematically illustrating the spectrum shift during discharge.

In the case of the present invention, the current density in the flashlamp is not controlled but develops itself in a free discharge, as illustrated in FIG. 2. FIG. 4 is a graph comparable to FIG. 2, also illustrating schematically the shift of the spectral energy distribution as a function of time during the current pulse, and illustrating that this shift is in synchronisation with the momentaneous current density in the current pulse. While the graph is just schematical, it can be seen that, with time, this energy distribution shifts to a region where the beneficial effect of hair removal is reduced and potentially harmful effects are increased. Further, since the aim of the apparatus is hair removal, the energy in the spectral region not contributing to hair removal is basically wasted energy. Further, the high energy consumption leads to heating of the system components and calls for cooling systems of increased capacity.

The improvement proposed by the present invention basically is a surprisingly simple measure: the discharge is interrupted before the natural extinction time t2 is reached. Consequently, it is avoided to generate light associated with the lower current levels that would have occurred after the interruption moment: all energy output is dedicated to the higher current levels before the interruption moment.

Figure 5:
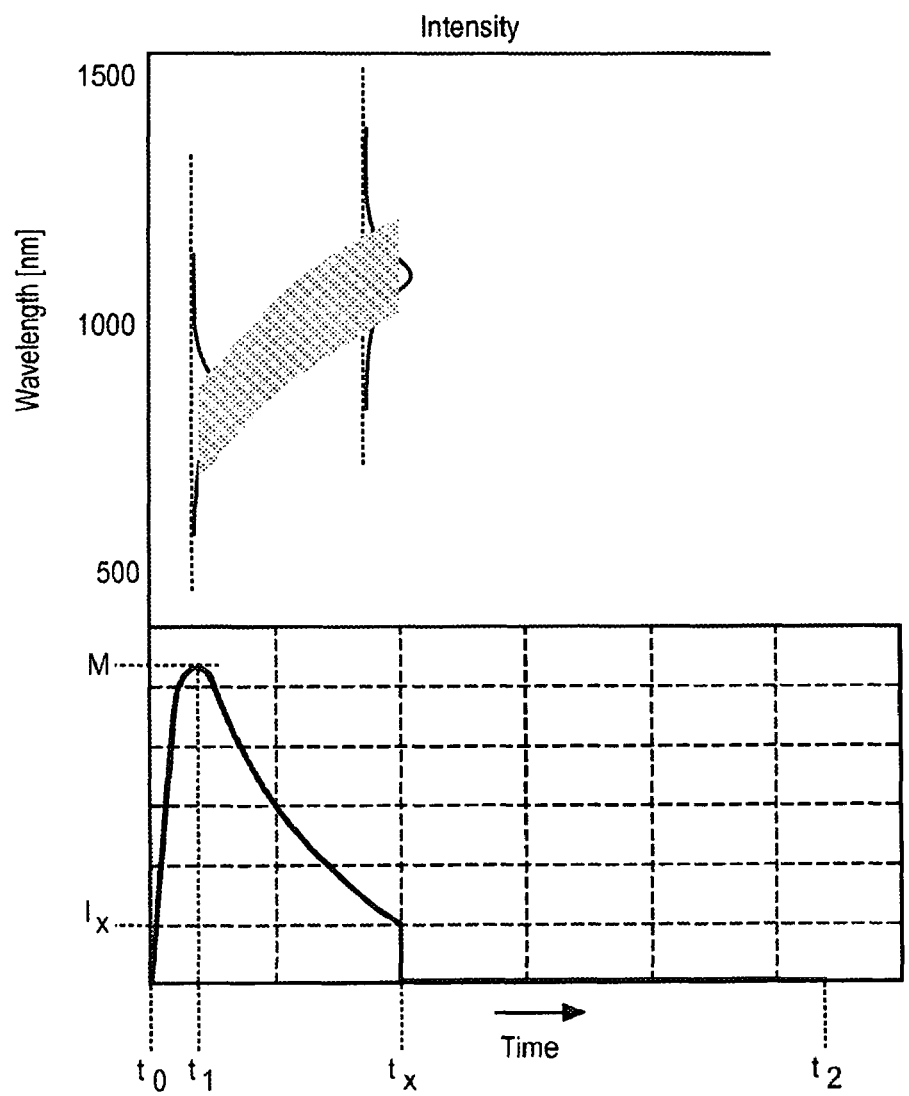
FIG. 5 is a graph comparable to FIG. 4 for the situation where the current is cut in accordance with the present invention.

For a system of nominal design, the invention is implemented such that the control device 6 opens the switch 5 when the current density drops below a threshold level Ix, which happens at a time tx before t2. This is illustrated in FIG. 5, which is a graph comparable to FIG. 4. As a result of the switch 5 being opened, the current is immediately cut down to zero and the light pulse is immediately ended. According to the invention, the discharge current is allowed to continue as long as the spectrum of the generated light contains sufficient energy in the beneficial regions 1 and 2, and is discontinued when the energy is mainly spent in region 3. Thus, the waste of energy is minimized, cooling requirements are reduced, and pain sensation is reduced.

The precise value of Ix is not critical, even for one specific skin treatment system, i.e. a specific combination of lamp, capacitor and charging voltage. When making some assumptions, it will be possible to define an optimum value for Ix, but this optimum may be different for different systems. Further, such optimum value may differ for different skin types, and the control device 6 may be provided with a user input device 7, for instance a rotating knob or a press button, for inputting a skin type, and the control device 6 may amend its interruption settings on the basis of the inputted skin type.

Further, an embodiment of the system according to the present invention comprises current density measuring means, but in practice it may be difficult for the control device to actually measure the current density and to switch off the current when the current density passes the density threshold. Therefore, in another embodiment which is easier to implement, the system comprises a current sensor for sensing the lamp current, and the control device calculates the current density using data relating to the lamp or, alternatively, the current density threshold is translated to a threshold for the lamp current magnitude for the specific lamp. In yet another embodiment which is even easier to implement, the system comprises time measuring means and the control device monitors the time lapsed since t0 (or since t1) and opens the switch 5 to switch off the current at time tx.

Time tx can be calculated in advance by the manufacturer, by measuring the lamp current as a function of time, and (?) converting the lamp current to current density on the basis of knowledge of the lamp design. From a basic relationship between current density and spectrum, the manufacturer can decide at which current level he wishes to cut the current, and from said measurements he can find the corresponding time tx.

On the other hand, it is also possible, in a specific system configuration, to perform an experiment by varying the cutoff time tx and measuring the resulting overall treatment spectrum. By deciding which spectrums are acceptable and which spectrums are not, a choice for tx results. The precise criterion used to decide which spectrums are acceptable and which spectrums are not may depend on the individual manufacturer. For a possible criterion, it is possible to determine the momentary energy contents in a first spectral region, for instance the region 550-950 nm, and to determine the momentary energy contents in a second spectral region, for instance the region of 950 nm and above, to calculate the ratio between these two measured contents, and to cut the current when the ratio is above a certain value, for instance 50%, in favor of the second region.

In any case, while it may be possible to define an optimal moment for cutting the current, it is noted that the present invention already provides an advantage if the current is cut at any time between t1 and t2. Further, the inventors have tested some practical combinations of xenon lamp, capacitor and charging voltage, and found that in all of the tested combinations the optimal cutting moment tx was in the range between 1.5 ms and 2.0 ms, so even without performing experiments it seems justified to select tx in said range.

In another elaboration, the present invention provides a system of supra-nominal design, meaning that, as compared to the nominal design of FIG. 2 and FIG. 4, the current level is higher and the natural extinction time t2' is later than time t2 indicated in FIG. 2. Starting from the nominal design explained above, a supra-nominal design can be obtained by increasing the capacitance value of the capacitor 4. This increased capacitance value will be indicated as $C_1$. It should thus be clear that, if the capacitor were allowed to freely discharge over the lamp, i.e. until natural extinction time t2', the energy $E_{SKIN}$ input into the skin would be higher than the assumed maximum $E_M$. In this system of supra-nominal design, according to the present invention, the control device 6 opens the switch 5 so as to interrupt the discharge at a time $t_E$ earlier than the natural extinction time t2 of the nominal design, wherein the interruption time $t_E$ is set such that the total amount of energy $E_{SKIN}$ applied to the skin is smaller than, or equal to, the maximum amount $E_M$.

Figure 6:
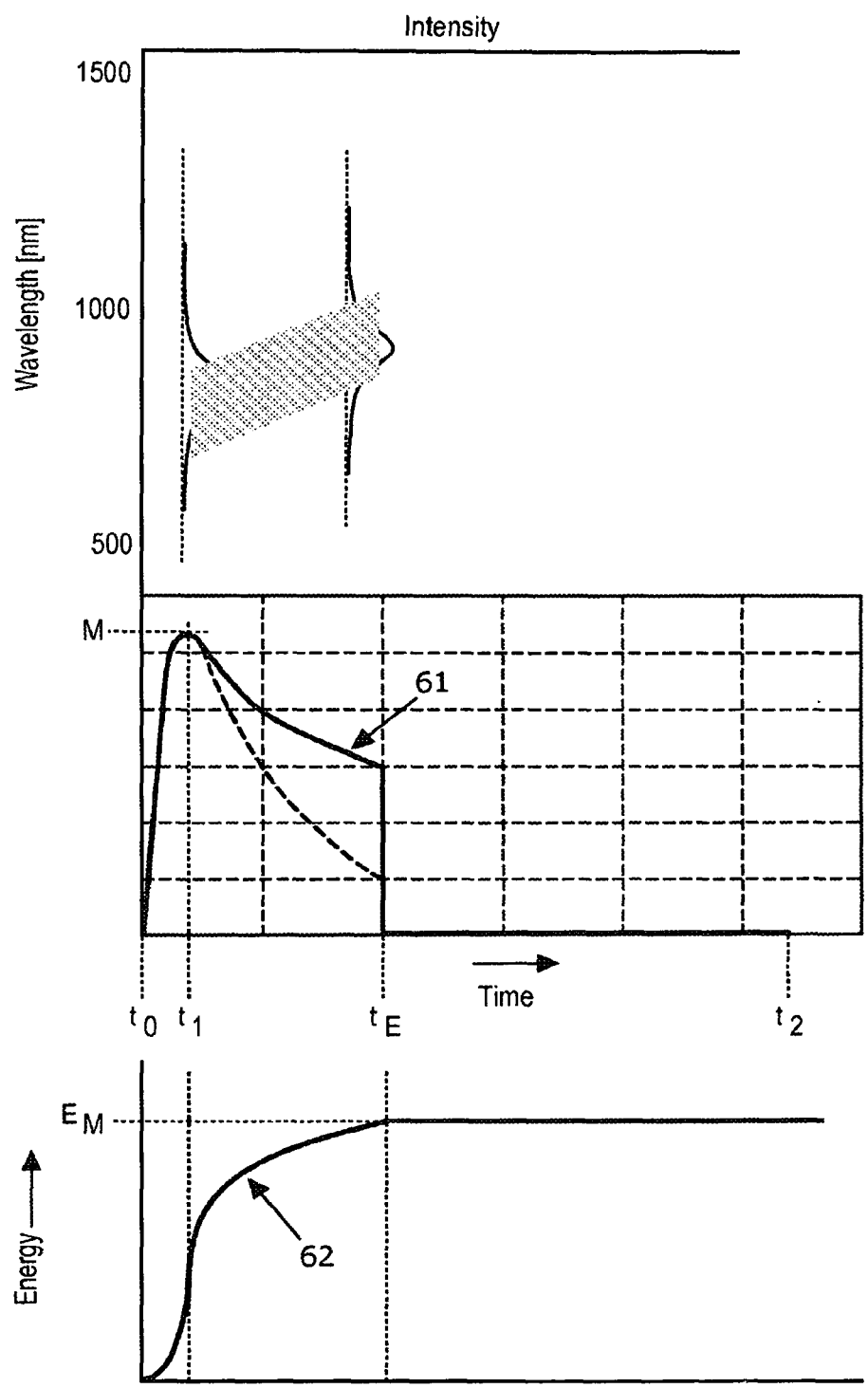
FIG. 6 is a graph comparable to FIG. 5.

This mode of operation is illustrated in FIG. 6, which is comparable to FIG. 5. Curve 61 indicates the lamp current (or current density) as a function of time (arbitrary units). The dotted line indicates the current for the comparable nominal design of FIG. 2 and FIG. 4. It can be seen that, after the current maximum M, the current is higher than in the nominal design. In fact, even the current maximum itself may be higher, but this is not shown. Curve 62 indicates the accumulated energy $E_A$ applied to the skin as a function of time; basically, curve 61 is proportional to the derivative of curve 62. In this example, the applied energy $E_A$ equals the maximum energy $E_M$ at time $t_E$. At that moment, the discharge current is cut off, so that the light input into the skin becomes zero.

In this method according to the present invention, it is assured on the one hand that the maximum allowable energy input into the skin is not surpassed, while on the other hand the discharge in the lamp is executed with increased current so that, during the light flash, the light mainly consists of useful wavelengths and the proportion of unuseful or even harmful wavelengths has been reduced. Since there is a higher output of "useful" frequencies, a more effective hair removal results.

In one possible embodiment of the present invention, the control device 6 is provided with a current sensor (not shown) to sense the lamp current as a function of time, and perhaps even a voltage sensor (not shown) to sense the lamp voltage as a function of time so as to be able to calculate lamp power as current multiplied by voltage. In a memory 8, the control device 6 has information defining the energy maximum $E_M$. During operation, the control device 6 monitors the energy $E_A$ outputted by the lamp as a function of time, by integrating the calculated lamp power (i.e. measured current multiplied by measured voltage or measured current multiplied by an assumed fixed lamp voltage value) over time, and compares this with the energy maximum $E_M$. When the control device 6 finds that the applied energy $E_A$ reaches the maximum $E_M$, it opens the switch 5.

In another embodiment, the control device 6 is provided with a voltage sensor (not shown) to sense the capacitor voltage as a function of time. At all times during discharge, the momentary capacitor voltage $V_R$ corresponds to the amount of energy $E_R$ remaining in the capacitor in accordance with $E_R = 0.5 \cdot V_R \cdot C^2$, and thus the applied energy $E_A$ can easily be calculated as $E_A = E_C - E_R$.

In yet another embodiment, in an experimental stage, the manufacturer of the system performs tests to determine the time $t_E$ when the applied energy $E_A$ reaches the maximum $E_M$. Information defining this time is stored in a memory 8. During operation, the control device 6 simply monitors the time and opens the switch 5 when the time reaches $t_E$.

In all of said embodiments, it is possible that the system comprises a user input device 7 for allowing a user to input a signal indicating a skin type, while in the memory 8 data are stored corresponding to the respective skin types. On the basis of the skin type input received, the control device 6 retrieves the corresponding information from memory 8. Otherwise, operation is the same as described above.

It should be clear that the invention thus provides a saving in energy. Since the capacitor is not fully discharged, recharging the capacitor can be done faster and/or the requirements for the charging voltage source are reduced. Further, because the energy consumption is reduced, less energy is converted into heat.

Summarizing, a method of operating a flashlamp in a skin treatment system comprises the steps of establishing a conductive path between the flashlamp and a charged capacitor causing a free discharge within the flashlamp, and interrupting said conductive path such as to cut off the current through the lamp when the current density drops below a predetermined current density threshold level or when the energy applied to the skin reaches a certain maximum.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appending claims.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

In the above, the present invention has been explained with reference to block diagrams, which illustrate functional blocks of the device according to the present invention. It is to be understood that one or more of these functional blocks may be implemented in hardware, where the function of such a functional block is performed by individual hardware components, but it is also possible that one or more of these functional blocks are implemented in software, so that the function of such one or more functional blocks is performed by one or more program lines of a computer program or a programmable device such as a microprocessor, microcontroller, digital signal processor, etc.

What is claimed is:

1. A skin treatment method comprising the steps of:
   charging a capacitor to a known level of energy capacity;
   discharging the capacitor through a flashlamp at a first time, wherein said capacitor discharge initiating the flashlamp to output a light to a skin surface,
   monitoring an effect of an application of said light on the skin surface; and
   interrupting the discharge of the capacitor through the flashlamp based on achieving a desired application of said light on to the skin surface.

2. The method according to claim 1, wherein said desired application of light comprises:
   a spectrum of the outputted light possess insufficient energy in a desirable frequency region associated with said skin treatment.

3. The method according to claim 1, wherein said desired application of light comprises:
   a current density of the discharge of the capacitor through the flashlamp causing insufficient energy in a desirable frequency region of the outputted light.

4. The method according to claim 1, wherein said desired application of light comprises:
   a maximum desirable energy applied to said skin surface.

5. The method according to claim 1, further comprising the steps of:
   receiving a skin type from an input device; and
   adjusting said desired application of light based on the received skin type.

6. The method according to claim 5, wherein said input device comprises at least one of: a rotating knob or a button press.

7. The method according to claim 1, further comprising:
   discharging the capacitor, through the flashlamp, using a switch.

8. The method according to claim 7, interrupting the discharge of the capacitor through the flashlamp using the switch.

9. A hair removal treatment system comprising:
   a flashlamp;
   a capacitor connected in parallel with the flashlamp;
   a power source configured to charge the capacitor to achieve a known energy (Ec);
   a controllable switching device configured to:
     provide an electrical connection between said flashlamp and said capacitor;
   a control device configured to:
     connect the capacitor to the flashlamp, using the controllable switching device, after said known energy (Ec) stored in said capacitor is achieved, said connection to the capacitor representing a start time, (t0) to discharge the capacitor through the flashlamp, said discharge initiating the flashlamp to output a light to a skin surface; and
     disconnect the capacitor from the flashlamp, using the controllable switching device, to cut off the discharge of the capacitor through the flashlamp after an appropriate application of said light to said skin surface has been achieved.

10. The system according to claim 9, wherein said appropriate application of light comprises:
    a spectrum of the outputted light having insufficient energy in a desirable frequency region associated with skin treatment.

11. The system according to claim 9, said appropriate application of light comprises;
    a current density causing insufficient energy in a desirable frequency region of said outputted light associated with skin treatment.

12. The system according to claim 9, said appropriate application of light comprises:
    an energy applied to the skin surface being greater than a maximum desirable energy.

13. The system according to claim 9, wherein the flashlamp is a xenon lamp.

14. The system according to claim 9, wherein the controllable switching device comprises:
    a first switch configured to connect the capacitor to the flashlamp.

15. The system according to claim 14, the control device configured to:
    alternate a position of the first switch from one of: a first position and a second position.

16. The system according to claim 15, wherein the first position is a closed position and the second position is an open position.

17. The system according to claim 9, wherein the control device comprises:
   a memory configured to:
   store said an amount associated with said appropriate application of light.

18. The system according to claim 9, further comprising:
   an input device configured to:
   receive a skin type.

19. The system according to claim 18, wherein the appropriate application of light is based on the received skin type.

* * * * *